United States Patent [19]

Louvo et al.

[11] Patent Number: 5,043,905
[45] Date of Patent: Aug. 27, 1991

[54] AUTOMATIC METHOD FOR CONTROLLING A PROCESS MELT OF TWO-PHASE CAST BRASS

[75] Inventors: Arno Louvo, Helsinki; Tapio Rantala; Veijo Rauta, both of Espoo, all of Finland

[73] Assignee: Valtion Teknillinen Tutkimuskeskus, Vuorimiehentie, Finland

[21] Appl. No.: 362,884

[22] Filed: Jun. 7, 1989

Related U.S. Application Data

[63] Continuation-in-part of Ser. No. 26,591, Mar. 17, 1987, abandoned, which is a continuation of Ser. No. 623,442, Jun. 22, 1984, abandoned.

[30] Foreign Application Priority Data

Jun. 30, 1983 [FI] Finland .................. 832398

[51] Int. Cl.⁵ .................. G06F 15/46; G01N 25/02
[52] U.S. Cl. .................. 364/472; 148/2; 364/497; 364/557; 374/26
[58] Field of Search .................. 364/472, 496–500, 364/557; 148/1, 2, 3, 11.5 R, 434; 164/4.1, 451–454; 266/80; 374/25, 26

[56] References Cited

U.S. PATENT DOCUMENTS

| | | | |
|---|---|---|---|
| 3,963,526 | 6/1976 | Lunn | 148/11.5 X |
| 4,088,974 | 5/1978 | Zhitetsky et al. | 364/499 X |
| 4,187,541 | 2/1980 | Skurikhin et al. | 364/497 |
| 4,198,679 | 4/1980 | Fainzilberg | 374/26 X |
| 4,443,118 | 4/1984 | Cure | 374/26 |

Primary Examiner—Joseph Ruggiero
Attorney, Agent, or Firm—Kenyon & Kenyon

[57] ABSTRACT

Method for controlling a process melt of two-phase cast brass, whereby the cast properties of said process melt, the dezincification resistance of the piece cast from said melt and the required analysis corrections can be estimated. The method according to the invention is based on phase transformations in the brass occurring during solidification and cooling, on effective Cu percentage and on measurement and interpretation of the cooling curve by means of a computer which writes out the conclusions it has drawn about the quality of the melt and recommends the needed analysis corrections, whereby the alloying elements are copper, zinc and aluminum. A sample of the melt to be analyzed is poured into a crucible (A) which has a thermoelement (A1) and which is insulated (A3). From the crucible a compensation cable leads to the measuring unit (B) from which the measurement information is transferred to the microcomputer (C) controlling the measurement, treating the measurement information and writing out on the display (E) and/or the printer (F) an estimate of the melt properties, the most important phase transformations noted, the deviation of the melt from the effective Cu percentage and the analysis correction directions.

3 Claims, 7 Drawing Sheets

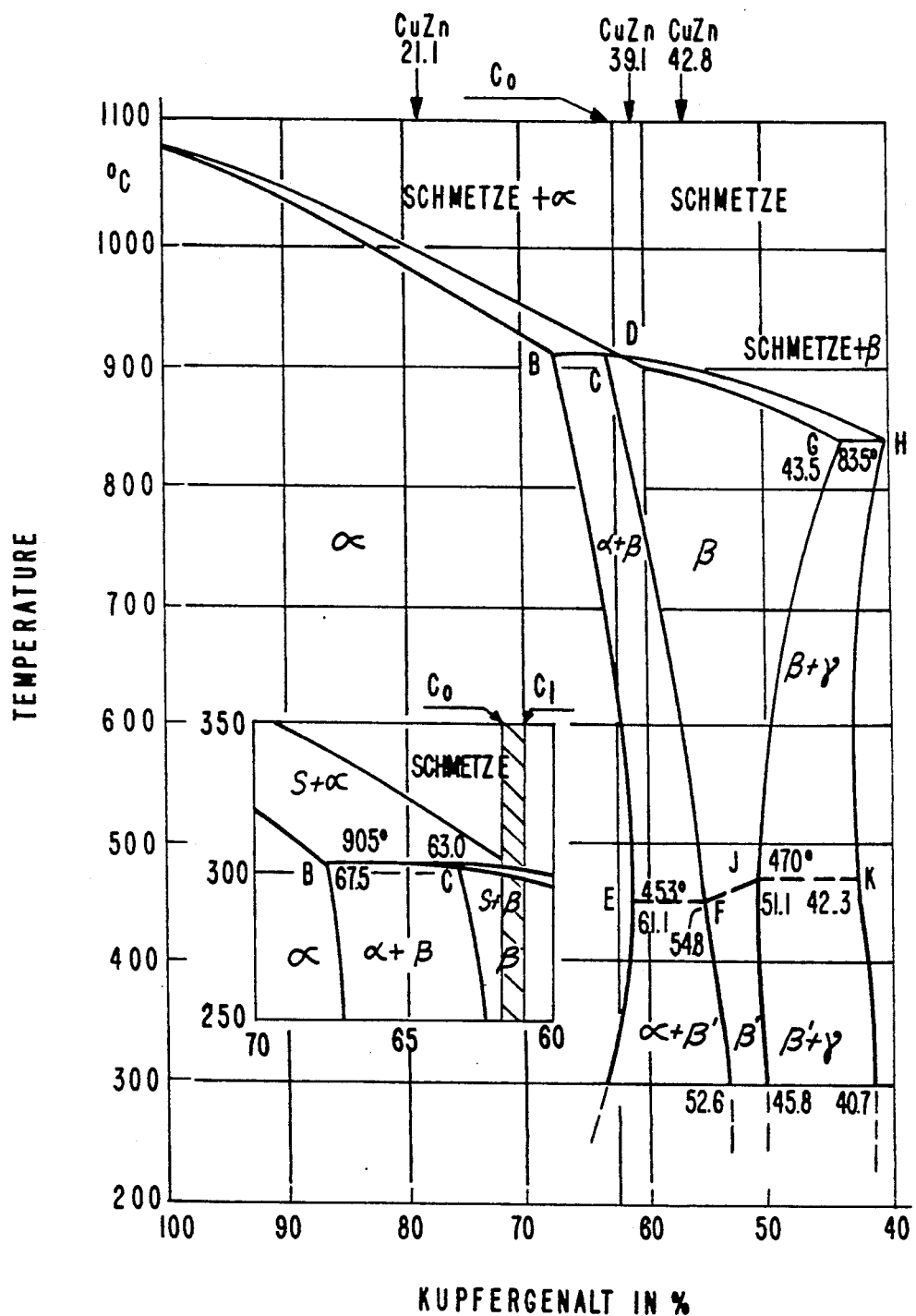
F I G. 1

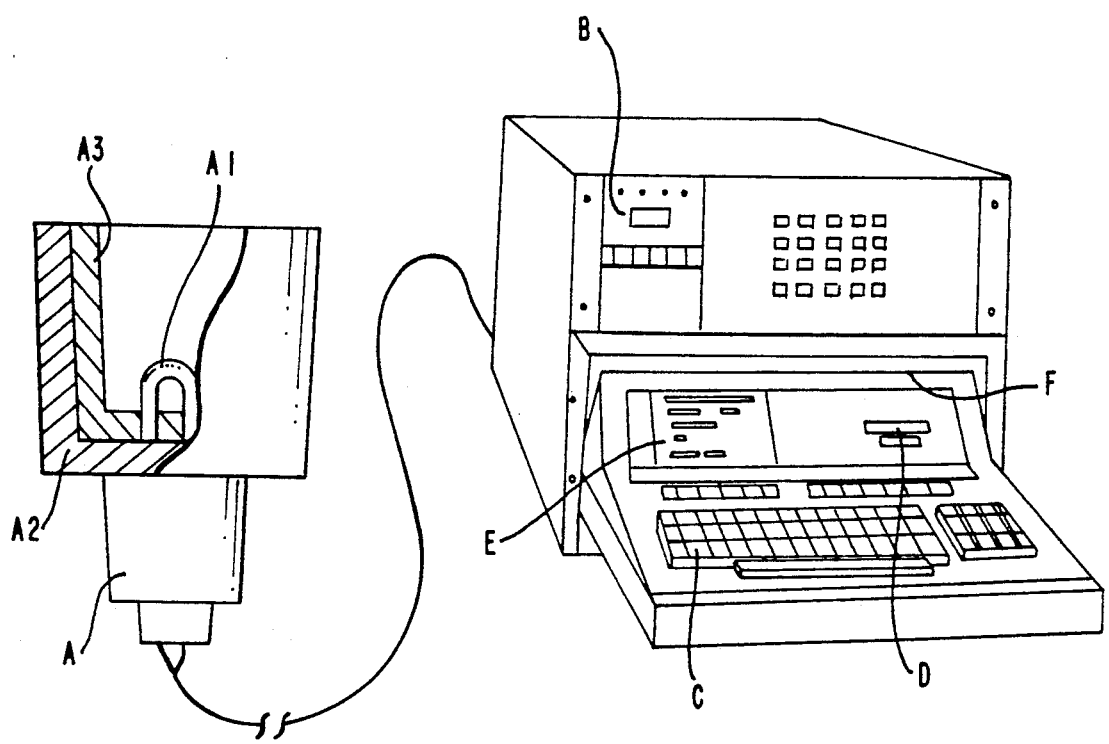
F I G. 2

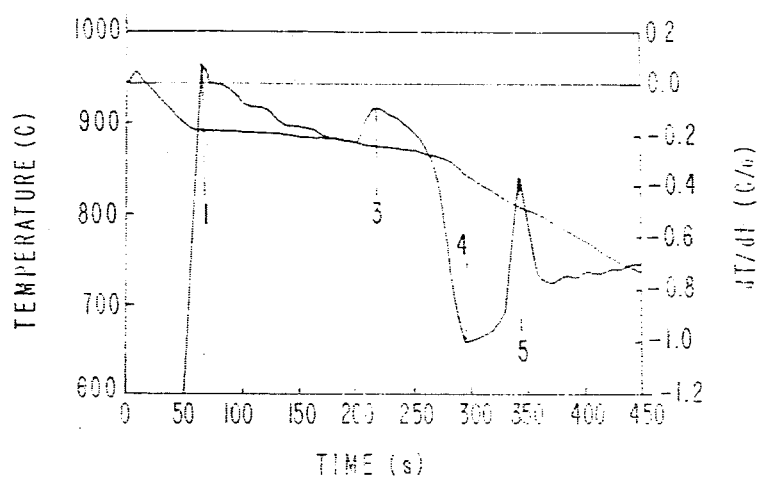
FIG. 3a
THERMAL ANALYSIS OF THE MELT AT ...
REACTIONs→∝ OCCURRED
CASTABILITY AND CORROSION
PROPERTIES OF BRASS ARE GOOD
CUE IS 0.04 PERCENTAGE BELOW THE
OPTIMUM- ADD 0.2% COPPER (THE YIELD
IS SUPPOSED TO BE 100%)
FIG. 3b
FIG. 3c

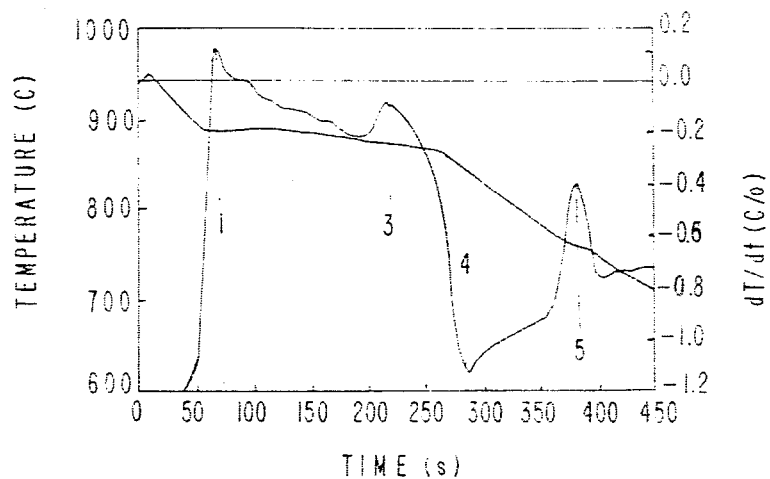
FIG. 4a
THERMAL ANALYSIS OF THE MELT AT 10:45
REACTION s-α OCCURRED
THE COMPOSITION OF BRASS IS OUTSIDE OF THE LIMITS
CUE IS 0.97 PERCENTAGE BELOW THE OPTIMUM— ADD 2.92% COPPER (THE YIELD IS SUPPOSED TO BE 100%
FIG. 4b
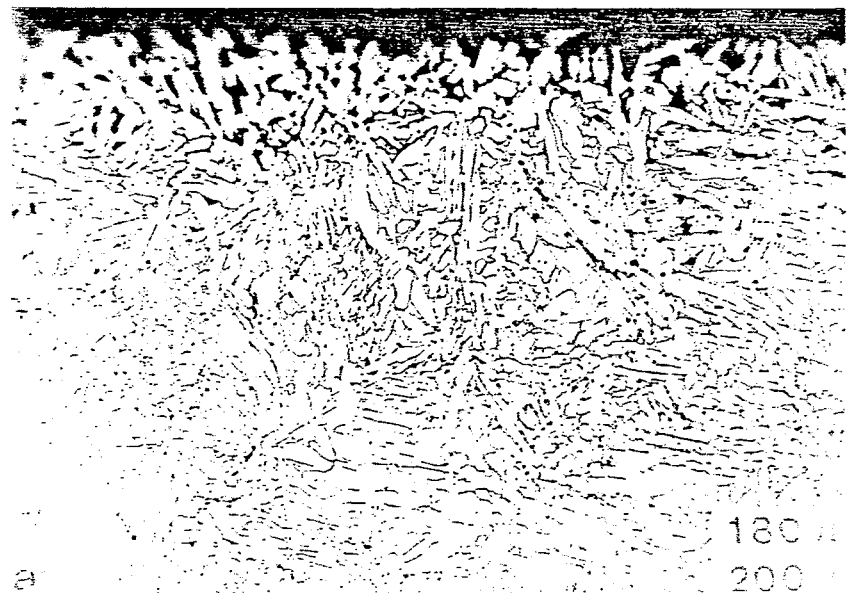
FIG. 4c

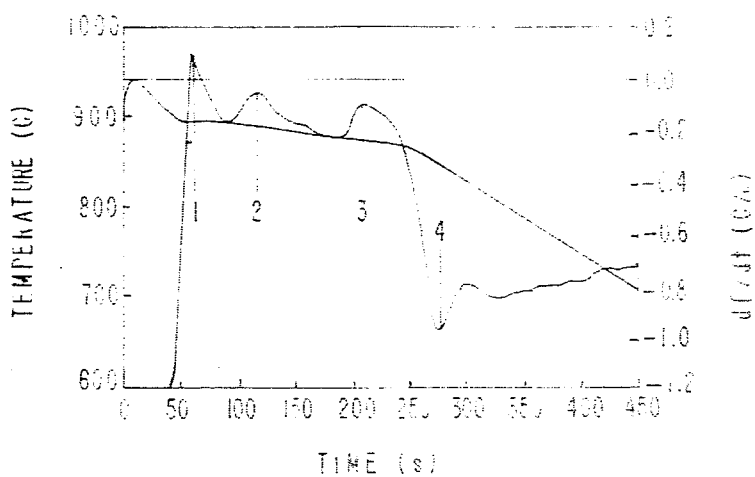
FIG. 5a
THERMAL ANALYSIS OF THE MELT AT 910
PERITECTIC REACTION OCCURRED
THE COMPOSITION OF BRASS IS OUTSIDE OF THE LIMITS
CUE IS 0.43 PERCENTAGE OVER THE OPTIMUM—ADD 0.72% ZINC (THE YIELD IS SUPPOSED TO BE 100%)
FIG. 5b
FIG. 5c

AUTOMATIC METHOD FOR CONTROLLING A PROCESS MELT OF TWO-PHASE CAST BRASS

RELATED APPLICATION

This application is a continuation-in-part of co-pending application Ser. No. 026,591, filed Mar. 17, 1987, abandoned, which is a continuation of application Ser. No. 623,442, filed June 22, 1984, which has been abandoned.

FIELD OF INVENTION

The method according to the invention relates to phase transformations of cast brass, where these transformations are analyzed with a microcomputer from a process melt by means of thermal analysis. On the basis of the computer analysis the composition of the melt is corrected so that castability is good and that the piece has the optimum microstructure.

BACKGROUND OF THE INVENTION

Castings of said brass are used in valves, water pipes and pipe connections of water installations etc., whereby dezincification resistance is one of the most important requirements of the material. This property is tested with an accelerated dezincification test according to the standard SFS 3873.

In practice the structure has been found dezincification resistant, when the $\alpha$-phase of brass is inhibited, e.g. with arsenic, to be dezincification resistant, and the $\beta$-phase in the structure susceptible to dezincification is uniformly distributed in the structure. The effective Cu percentage of brass with a given cooling rate influences in the first place the decomposition of the $\beta$-phase.

The effective Cu percentage has also a decisive effect on the castability of the alloy (fluidity, surface checkings and shrinkage). When realizing good castability and dezincification resistance the effective Cu percentage can only vary within very narrow limits.

In order to obtain said properties, chill casting processes use ingots intended for dezincification resistant castings and return scrap from said process as raw material for the melt.

In practice zinc volatilizes from the melt in a continuous melting process, and often a part of the aluminum functioning as an alloying element is oxidized. Hereby the effective Cu percentage of the melt increases. An abundant use of return scrap has also an effect, because the Zn and Al percentages of the scrap have decreased in earlier meltings. Thus, without analyzers the foundries have difficulties in knowing the composition of the process melt and in making analysis corrections.

Many foundries do not have analyzers with which the chemical composition of the melt could be determined. On the other hand, the analysis processes in use are slow and the analysis accuracy obtained with these is not always sufficient in view of calculating the effective Cu percentage. Especially when the errors in the percentages of different elements cumulate, the error in the effective Cu percentage can be of the same order as the allowed variation. With the analysis processes in use, the analysis correction directions of the melt cannot either be automatically obtained. As a drawback of the determination of the effective Cu percentage based on the elementary analysis can also be considered that there is not fully an unanimity about the coefficients (Zn equivalents for the different elements) in the calculation formula for the effective Cu percentage.

One important advantage of the invention can be is that the effective Cu percentage of the melt can be determined automatically and quickly. and simultaneously the alloying element calculated according to the method for correcting the composition of the melt can be made so that the cast properties are optimal and the castings are dezincification resistant. It must be particularly stressed that the analysis with its possible correction directions is obtained before using the melt. The analysis is also clearly more trustworthy than what can be obtained with the processes in use.

BRIEF DESCRIPTION OF THE DRAWINGS

FIG. 1 is a diagram of the Cu-Zn binary phase whose phase transformation temperatures are analyzed by the inventive method for purposes of optimizing the composition of the melt necessary for good castability and optimum microstructure. On the phase diagram the biggest allowed effective Cu percentage is denoted with $C_0$. From this composition the deviation can be 0.7% units from $C_0$ to the right to the composition $C_1$.

FIG. 2 is the arrangement of measuring components. Said Fig. discloses the measuring components to be used: casting crucible (A), measuring unit (B), microcomputer (C), cassette position (D), display (E) and printer (F).

FIGS. 3 to 5 are sample melt compositions wherein:
subfigure a) illustrates the derived melt cooling curve;
subfigure b) is the microcomputer writing of the thermal analysis; and
subfigure c) is the microstructure of the solidified melt.

PREFERRED EMBODIMENT

The manner of carrying out the analysis is best implemented as follows: The molten brass is poured into a casting crucible (A) which is insulated on its inner surface so that the cooling rate before reaction is less that 3° C. per second and the cooling time about 250 seconds. A thermoelement (A1) placed in the thermal centre of the crucible, registers the temperature which is transferred through the measuring unit (B) to the microcomputer (C). The cooling curves are derived from mathematical computation using the following standard formulas.

1. The time derivative of temperature (dT/dt) is calculated by the least square method:

$$T = \frac{dT}{dt} = \frac{n\, tT - t\, T}{n\, t^2 - (t)^2}$$

T = temperature
t = time
n = number of points

2. The second time derivative (d(dT/dt)) is calculated in similar way as the first time derivative (eq. 1).

$$\frac{dT}{dt} = \frac{n\, tT - t\, T}{n\, t^2 - (t)^2}$$

3. The analysis of curves is explained using the flowchart for the analysis subroutine.

Figure 6:
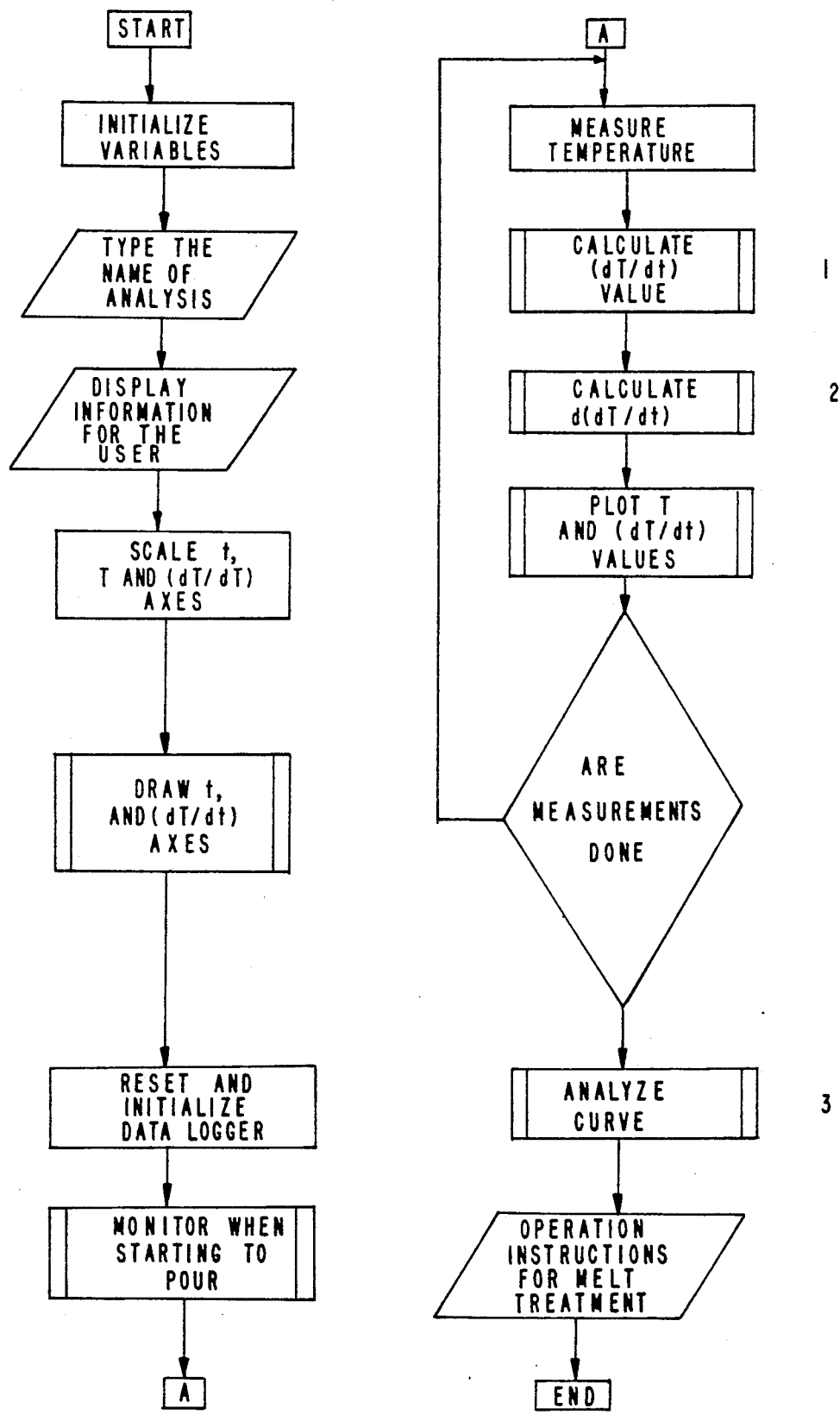
FIGS. 6 and 7 are flow diagrams of the algorithms performed by the microcomputer.

The computer (C) implements the methods shown in FIG. 6 by first registering the change in temperature as a function of time and derives the thus obtained cooling curve two times during the measuring. After this the computer (C) determines the appearing phase transformations, their temperatures and reciprocal points in time, on the basis of which it calculates the effective Cu percentage. The machine compares the Cu percentage obtained from the analysis with the optimum percentage, and writes out (E, F) the required alloying addition (Cu, Zn, Al). The whole analysis takes about 8 minutes.

Figure 7:
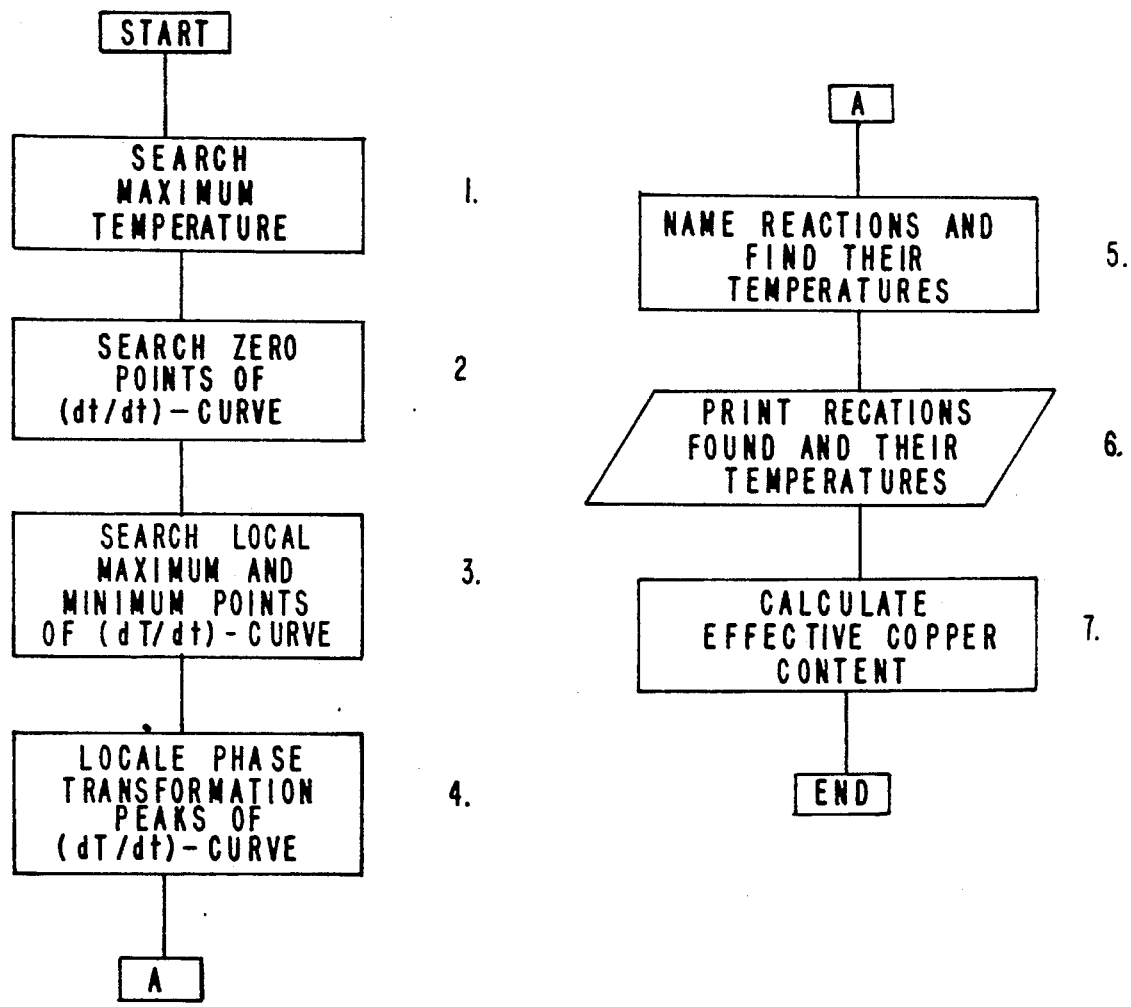

The microcomputer (C), upon receiving the registered temperature value, performs the seven step algorithm set forth in FIG. 7 calculated by formulas which are known in the art of metallurgical phase transformation. See Savitzky et al. "Smoothing And Differentiation Of Data By Simplified Least Squares Procedures" *ANALYTICAL CHEMISTRY* Vol. 36, No. 8 July, 1964 pp. 1627-1639; Ekpoom et al. "Thermal Analysis By Differential Heat Analysis (DHA) Of Cast Iron", *AFS TRANSACTIONS* 1981, page 27-38.

Step 1 requires the microcomputer (C) to search the cooling curve for the maximum temperature Tmax and its equivalent time t(Tmax). This point on the curve, t(Tmax), is used as a starting point for the analysis.

In step 2, the microcomputer (C) searches the (dT/dt) curve for its zero points by locating the points where the slope of the curve changes its sign.

In step 3, the microcomputer (C) searches and locates the local maximum and minimum points on the (dT/dt) curve by locating the zero points of the (dT/dt) curve.

In step 4, the phase transformation peaks of the (dT/dt) curve are selected by comparing the difference between the minimum and maximum points located beside each other.

In step 5, the microcomputer (C) assigns names to the reactions and determine their temperature according to following specific criteria. The solidus is named at the global minimum value of the (dT/dt) curve. If three significant peaks are found before solidus, the reactions are liquidus (alpha phase), peritectic and monotectic reaction. In such reactions, the effective copper content is over $C_0$ (refer to FIG. 1). If two significant peaks are found before solidus, the reactions are liquidus (beta phase) and monotectic reaction. In such reactions, the effective copper content is under $C_0$. If only one significant peak is found after solidus, the reaction is an alpha/beta reaction. Similarly, in this reaction, the effective copper content is under $C_0$. By knowing the location (index) of this peak, the temperature value T (alpha/beta) can be picked from the cooling curve (Tcurve).

In step 6, the effective copper content is calculated using the following equations:

$$P1 = (P-L)/(S-L)$$

$$A1 = (A-L)/(S-L),$$

where
t = time
p = t(peritectic reaction)
S = t(solidus)
L = t(liquidus)
A = t(alpha/beta reaction)

$$K1 = a + b \times P1 \text{ (if peritectic reaction found)}$$

$$K2 = c + d \times A1 \text{ (if alpha/beta reaction found)}$$

$$K3 = e + f \times T(A) \text{ (if alpha/beta reaction found)}$$

$$K = (K1 + K2 + K3)/3.$$

where
K = effective copper content
T(A) = temperature of the alpha/beta reaction

| a = 60.1 | b = 8.81 |
| c = 66.3 | d = −3.61 |
| e = 46.3 | f = 0.0195 |

In step 7, instructions to correct the melt composition are calculated using the following equations:

a) If K is over the limit K(max) = 62.25%, Zn has to be added to reach the target composition (a little bit under the optimum). Need of zinc, Zn(need) expressed as the percentage of the charge is as follows:

$$Zn(need) = -100 \times S/(S + Cu(ave)).$$

where
$S = Const \times (K(target) - K))$
Const = 1.05
Cu(ave) = 64% (average copper content of brass)
K(target) = 62.0% (optimum composition is 62.25%)

b) If K is under the limit K(max) = 61.55%, Cu has to be added to reach the target composition (a little bit under the optimum). Need of Copper, Cu(need) expressed as the percentage of the charge is as follows:

$$Cu(need) = -100 \times S/(S + Cu(ave)) - 100).$$

where the unknowns are as above

FIGS. 3a to 5c show examples of analysis results in cases where the effective Cu percentage is at the right composition range, too small, or too big. The corresponding microstructures and writing out of the computer analysis for each case are also shown in the Figs. FIG. 3c is a microstructure figure (enlargement 200×) of two-phase brass. The microstructure is optimal from the viewpoint of cast properties and dezincification. In said structure the average dezincification depth has been only 70 m. FIG. 3a shows the curves of the derivative thermal analysis - cooling curve T = f(t)(G) and its first derivative curve dT/dt = f(t) (H). The first peak (1) in the cooling rate curve is a liquidus peak (solidification of the metal alloy begins). After this a monotectic reaction (3) between copper and lead (Pb 1.5%) occurs. To said brass a little lead is added in order to improve machinability. At point (4) the whole melt is solidified. After this the reaction (5) still occurs in the solid phase. FIG. 3b shows the writing out of the computer analysis. The effective Cu percentage is in the range of $C_1$-$C_0$ (FIG. 1).

The dezincification in the microstructure in FIG. 4c has proceeded to an average depth of 180 m. FIG. 4a shows the same reactions as FIG. 3a. The reaction (5) has occurred at a lower temperature than in the structure in FIG. 3c. The computer recommends an analysis correction. The effective Cu percentage is smaller than $C_1$.

The microstructure in FIG. 5c is especially bad from the viewpoint of the advancing dezincification: the depth of dezincification has been 380 m on an average. Reaction does not show in FIG. 5a any more. On the other hand a new "peak" (2) has appeared between "peaks" 1 and 3. This is caused by a peritectic reaction (2). The computer has noted this fact and again recommends an analysis correction. The effective Cu percentage is bigger than $C_0$.

The description and claims describe only some embodiments of the method according to the invention. The adaptations of the method according to the invention can vary even considerably within the scope of the claims.

We claim:

1. Method for correcting the analysis of a process melt of a two-phase cast brass for optimal castability and dezincification resistance, comprised of:
   determining the phase change temperatures in a brass melt by use of a thermoelement coupled to a microcomputer;
   determining the brass melt composition by comparison of its phase change temperature with phase change temperatures of known compositions stored within the microcomputer; and
   determining the amount of additional alloying elements required for achieving optimal brass melt composition range stored within the microcomputer.

2. Method for correcting the analysis of a process melt of a two-phase cast brass for optimal castability and dezincification resistance, comprised of:
   pouring a melt sample into a casting crucible having a diameter/height ratio of 1, having in its thermal center a thermoelement, and insulated such that the melt cooling rate before reaction is less than 30C per second and the cooling time is about 250 seconds;
   determining the phase change temperatures in the brass melt by use of a microcomputer coupled to the thermoelement;
   determining the brass melt composition by comparison of its phase change temperature with phase change temperatures of known compositions stored within the microcomputer; and
   determining the amount of additional alloying elements required for achieving optimal brass melt composition range stored within the microcomputer.

3. Method for correcting the analysis of a process melt of a two-phase cast brass for optimal castability and dezincification resistance, comprised of:
   determining the phase change temperatures in a brass melt by use of a thermoelement coupled to a microcomputer;
   determining the brass melt composition by comparison to its phase change temperature with phase change temperatures of known compositions stored within the microcomputer;
   determining the amount of additional alloying elements required for achieving optimal brass melt composition range stored within the microcomputer; and
   controlling the solidification structure of the process brass melt by addition of an inhibitor in a quantity resulting in needle-shaped crystalline structure, encapsulation of the $\beta$-phase by the $\alpha$-phase and minimalization of the mushy zone.

* * * * *